US00PP15325P2

(12) United States Plant Patent
Westhoff

(10) Patent No.: US PP15,325 P2
(45) Date of Patent: Nov. 16, 2004

(54) ***CALIBRACHOA* PLANT NAMED 'WESCACHERRYNO'**

(50) Latin Name: ***Calibrachoa* sp.**
Varietal Denomination: Wescacherryno

(75) Inventor: Heinrich Westhoff, Südlohn (DE)

(73) Assignee: Josef & Heinrich Westhoff Gartenbau-SpezialKulturen, Südlohn (DE)

( * ) Notice: Subject to any disclaimer, the term of this patent is extended or adjusted under 35 U.S.C. 154(b) by 0 days.

(21) Appl. No.: 10/759,724

(22) Filed: Jan. 16, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—June Hwu
(74) *Attorney, Agent, or Firm*—C. A. Whealy

(57) ABSTRACT

A distinct cultivar of *Calibrachoa* plant named 'Wescacherryno', characterized by its cascading and uniform growth habit; freely branching habit; dense and bushy plant habit; medium-sized flowers; and numerous red-colored flowers.

1 Drawing Sheet

Botanical classification/cultivar designation: *Calibrachoa* sp. cultivar Wescacherryno.

BACKGROUND OF THE INVENTION

The present Invention relates to a new and distinct cultivar of *Calibrachoa* plant, botanically known as *Calibrachoa* sp., and hereinafter referred to by the cultivar name 'Wescacherryno'.

The new *Calibrachoa* is a product of a planned breeding program conducted by the Inventor in Südlohn, Germany. The new *Calibrachoa* originated from a cross-pollination made by the Inventor of a proprietary selection of *Calibrachoa* identified as code number 01P206, not patented, as the female, or seed, parent with a proprietary selection of *Calibrachoa* identified as code number 01P136, not patented, as the male, or pollen, parent. The new *Calibrachoa* was discovered and selected by the Inventor in a controlled environment in Südlohn, Germany as a single plant within the resulting progeny from the above-mentioned cross-pollination in 2002.

Asexual reproduction of the new cultivar by terminal cuttings at Sudlohn-Oeding, Germany since 2002, has shown that the unique features of this new *Calibrachoa* are stable and reproduced true to type in successive generations.

SUMMARY OF THE INVENTION

Plants of the cultivar Wescacherryno have not been observed under all possible environmental conditions. The phenotype may vary with variations in environment such as temperature, light intensity and daylength without, however, any variance in genotype.

The following traits have been repeatedly observed and are determined to be the unique characteristics of 'Wescacherryno'. These characteristics in combination distinguish 'Wescacherryno' as a new and distinct cultivar:

1. Cascading and uniform growth habit.
2. Freely branching habit and relatively short internodes, dense and bushy plant habit.
3. Medium-sized flowers.
4. Numerous red-colored flowers.

Plants of the cultivar Wescacherryno can be compared to plants of the female parent selection. In side-by-side comparisons conducted in Südlohn, Germany, plants of the new *Calibrachoa* differed from plants of the female parent selection in the following characteristics:

1. Plants of the new *Calibrachoa* had smaller flowers than plants of the female parent selection.
2. Plants of the new *Calibrachoa* and the female parent selection differed in flower color as plants of the female parent selection had lighter red-colored flowers.

Plants of the cultivar Wescacherryno can be compared to plants of the male parent selection. In side-by-side comparisons conducted in Südlohn, Germany, plants of the new *Calibrachoa* differed from plants of the male parent selection in the following characteristics:

1. Plants of the new *Calibrachoa* had thinner stems than plants of the male parent selection.
2. Plants of the new *Calibrachoa* had smaller leaves than plants of the male parent selection.
3. Plants of the new *Calibrachoa* had larger flowers than plants of the male parent selection.

Plants of the new *Calibrachoa* can also be compared to plants of the *Calibrachoa* cultivar Wescacherry, disclosed in U.S. Plant Pat. No. 12,753. In side-by-side comparisons conducted in Südlohn, Germany, plants of the new *Calibrachoa* differed from plants of the cultivar Wescacherry in the following characteristics:

1. Plants of the new *Calibrachoa* had a more cascading plant habit than plants of the cultivar Wescacherry.
2. Plants of the new *Calibrachoa* had thinner branches than plants of the cultivar Wescacherry.
3. Plants of the new *Calibrachoa* had smaller flowers than plants of the cultivar Wescacherry.
4. Flower color of plants of the new *Calibrachoa* was more intense than flower color of plants of the cultivar Wescacherry.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Calibrachoa*.

The photograph at the top of the sheet comprises a side perspective view of typical flowering plants of 'Wescacherryno' grown in a hanging basket container.

The photograph at the bottom of the sheet is a close-up view of typical flowers of 'Wescacherryno'.

DETAILED BOTANICAL DESCRIPTION

Plants used in the aforementioned photographs and for the following description were grown under conditions which closely approximate commercial production conditions during the spring and summer in a glass-covered greenhouse in Südlohn, Germany. Plants were about 20 weeks from planting rooted cuttings and grown in 12-cm containers. During the production of the plants, the day temperatures ranged from 20 to 25° C., night temperatures ranged from 16 to 18° C., and light levels ranged from 3,000 to 50,000 lux.

In the following description, color references are made to The Royal Horticultural Society Colour Chart, 2001 Edition, except where general terms of ordinary dictionary significance are used.

Botanical classification: *Calibrachoa* sp. cultivar Wescacherryno.

Parentage:

*Female parent.*—Proprietary selection of *Calibrachoa* sp. identified as code number 01P206, not patented.

*Male parent.*—Proprietary selection of *Calibrachoa* sp. identified as code number 01P136, not patented.

Propagation:

*Type cutting.*—Terminal vegetative cuttings.

*Time to initiate roots.*—About 18 to 20 days at 20° C.

*Time to develop roots.*—About 20 to 28 days at 20° C.

*Root description.*—Numerous, fine, fibrous, and well-branched.

Plant description:

*Form.*—Annual flowering plant; cascading; uniform, rounded appearance, plants eventually become spherical in overall shape. Freely branching with lateral branches forming at every node. Vigorous growth habit.

*Usage.*—Appropriate for hanging baskets, window boxes and patio containers.

*Plant height* (*from soil level to top of plant plane*).—About 12 cm.

*Plant length* (*from soil level to lateral branches apices*).—About 70 cm.

*Plant diameter* (*area of spread*).—About 48 cm.

*Stem description.*—Main branches, length: About 60 cm. Main branches, diameter: About 1.9 mm. Lateral branches, length: About 20 to 42 cm. Lateral branches, diameter: About 1.2 mm. Internode length: About 1 cm. Texture: Densely pubescent. Strength: Strong, wiry. Color: 144B.

*Foliage description.*—Arrangement: Before flowering, alternate; after flowering, opposite; simple; sessile. Length: About 3.3 cm. Width: About 1.2 cm. Shape: Oblanceolate to elliptic. Apex: Rounded. Base: Attenuate. Margin: Entire. Aspect: Mostly flat. Texture, upper and lower surfaces: Pubescent. Venation pattern: Pinnate. Color: Developing foliage, upper surface: 137C. Developing foliage, lower surface: 137D. Fully expanded foliage, upper surface: 137A; midvein, 137B; lateral veins same as lamina. Fully expanded foliage, lower surface: 137C; midvein, 137C to 137D; lateral veins same as lamina.

Flower description:

*Flower type and habit.*—Medium-sized flowers; flowers face upright or outward; single, axillary. Flowers not persistent. Freely flowering with flowers forming at every axil.

*Natural flowering season.*—Spring until frost in the autumn; flowering continuous.

*Flower longevity on the plant.*—About one week.

*Flower size.*—Diameter: About 2.6 cm. Depth (height): About 2.1 cm. Tube length: About 1.9 to 2 cm. Throat diameter, distal end: About 9 mm. Tube diameter, proximal end: About 2 mm.

*Flower buds.*—Length: About 2.25 cm. Diameter: About 3 mm. Shape: Oblong. Color: Towards the apex, N77B; mid-section, 1C; towards the base, 1C with venation, 166A.

*Corolla.*—Arrangement/appearance: Single whorl of five petals, fused into flared trumpet. Petal length from throat: About 1 cm. Petal width: About 1.4 cm. Petal shape: Obtuse with rounded to cuspidate apex. Petal margin: Entire. Petal texture, upper and lower surfaces: Smooth, satiny. Color: Petal, when opening, upper surface: 46A. Petal, when opening, lower surface: 53B. Petal, fully opened, upper surface: 46B; venation, N186A; color becoming closer to 60A to 60B with development. Petal, fully opened, lower surface: 53C; venation, N77A. Flower throat (inside): 13A; venation, 166A; ring, N186A, about 3 mm in length. Flower tube (outside): 1B; venation, 166A.

*Sepals.*—Arrangement/appearance: Single whorl of five sepals, star-shaped. Length: About 1.8 cm. Width: About 3.2 mm. Shape: Lanceolate. Apex: Acute. Margin: Entire. Texture, upper and lower surfaces: Pubescent. Color, upper surface: 137A. Color, lower surface: 137B.

*Peduncles.*—Length: About 2 cm. Width: About 0.9 mm. Strength: Flexible, wiry. Color: 144A.

*Reproductive organs.*—Stamens: Quantity per flower: Five. Anther shape: Four-parted, oval. Anther length: About 2 mm. Anther diameter: About 1.2 mm. Anther color: 7A. Pollen amount: Scarce. Pollen color: 13A to 13B. Pistils: Quantity per flower: One. Pistil length: About 1.25 cm. Stigma shape: Oval. Stigma color: 143A to 143B. Style length: About 1.1 mm. Style color: 144C. Ovary color: 144C.

*Seed/fruit.*—Seed and fruit production has not been observed.

Disease/pest resistance: Plants of the new *Calibrachoa* have not been noted to be resistant to pathogens and pests common to *Calibrachoa*.

Temperature tolerance: Plants of the new *Calibrachoa* have been observed to be tolerant to temperatures ranging from 2 to 30° C.

It is claimed:

1. A new and distinct cultivar of *Calibrachoa* plant named 'Wescacherryno', as illustrated and described.

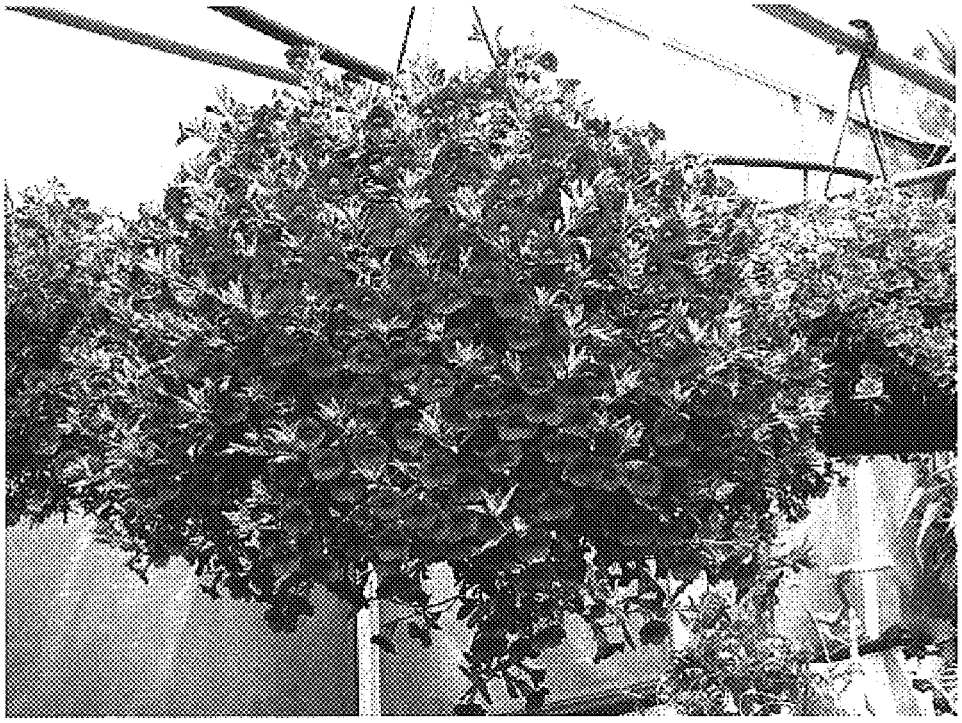
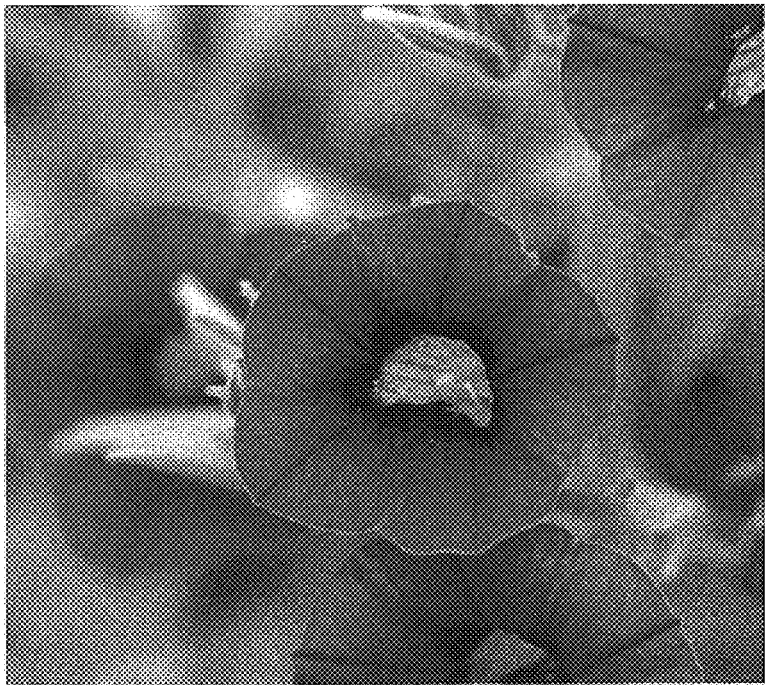

* * * * *